United States Patent [19]

Howe et al.

[11] Patent Number: 4,823,607
[45] Date of Patent: Apr. 25, 1989

[54] RELEASED FILM STRUCTURES AND METHOD OF MEASURING FILM PROPERTIES

[75] Inventors: Roger T. Howe, Lafayette, Calif.; Mehran Mehregany, Prairie Village, Kans.; Stephen D. Senturia, Boston, Mass.

[73] Assignee: Massachusetts Institute of Technology, Cambridge, Mass.

[21] Appl. No.: 51,526

[22] Filed: May 18, 1987

[51] Int. Cl.[4] ............................................. G01N 19/06
[52] U.S. Cl. ....................................................... 73/783
[58] Field of Search ................. 73/783, 787, 789, 762, 73/804

[56] References Cited

U.S. PATENT DOCUMENTS 3,994,598 11/1976 Reytblatt .......................... 73/762 X

OTHER PUBLICATIONS

Chapter 12, "Mechanical Properties of Thin Films", *Handbook of Thin Films Technology*, Maissel & Glang, ed., 1970.
*Measurement of Stress Generaged During Curing and in Cured Polyimide Films*, Geldermans, et al., IBM East Fishkill General Technology Division, Hopewell Junction, NY 12533, 1982.
*A Technique for the Determination of Stress in Thin Films*, Bromley et al, J. Vac. Sci. Technol. B, vol. 1, No. 4, Oct.-Dec. 1983.
*Stress in Polycrystalline and Amorhous Silicon Thin Films*, Howe and Muller, J. Appl. Phys. 54(8), Aug. 1983.
*A Simple Technique for the Determination of Mechanical Strain in Thin Films with Applications to Polysilicon*, Guckel, Randazzo, & Burns, J. Appl. Phys: 57(5), Mar. 1, 1985.
"Mechanical Properties of Thin Condensed Films", Hoffman, R. W. from *Physics of Thin Films*, 1966.
"Structure and Properties of Thin Films," Beams, J. W., from Proceedings of an International Conference held on 9/11/59, John Wiley & Sons, Inc., ed. by Neugelbauer, Newkirk and Vermilyea.
"Local Stress Measurement in Thin Thermal $SiO_2$ Films on Si Substrates", Lin, et al., J. Appl. Phys., vol. 43, No. 1, Jan. 1972.
"Deposition Techniques and Properties of Strain Compensated LPCVD Silicon Nitride Films," H. Guckel, D. K. Showers, D. W. Burns, C. R. Rutigliano, Wisconsin Ctr. for Applied Microelectronics, Dept. of Electrical & Computer Engineering, Univ. of Wisc.
"Novel Microstructures for the Study of Residual Stress in Polyimide Films," M. Mehregany, R. T. Howe, and S. D. Senturia in the Proceedings of the Electronic Materials Conference, Amherst, MA, 6/86, pp. 179-180.
"Novel Microstructures for the Study of Residual Stress in Polyimide Films," Mehregany, Howe, Senturia, in the Proceedings of the MIT VLSI Research Review, Cambridge, MA, May 19, 1986.

*Primary Examiner*—Jerry W. Myracle
*Attorney, Agent, or Firm*—Hamilton, Brook, Smith & Reynolds

[57] ABSTRACT

Released film structures are employed in measuring the mechanical properties of the film material. By measuring the deformation of thin film structures held under intrinsic tensile stress and then released, these mechanical properties can be accurately measured.

17 Claims, 8 Drawing Sheets

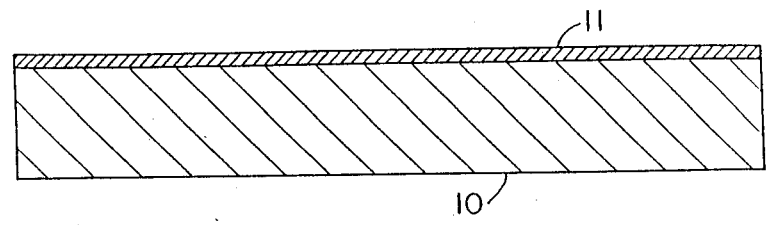
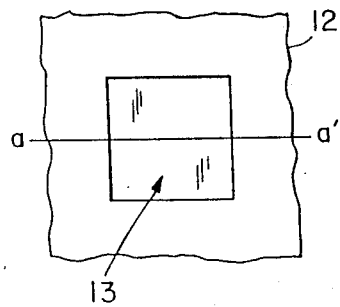
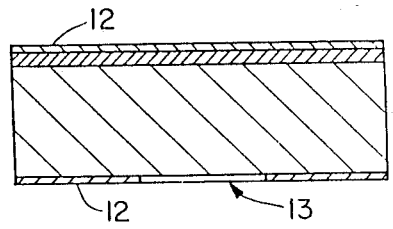
Fig. 1b
Fig. 1c
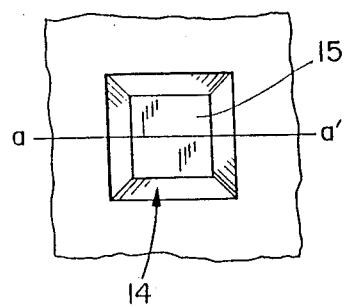
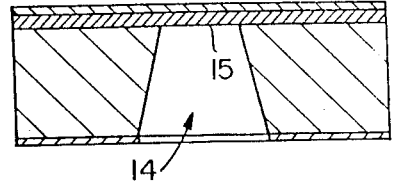
Fig. 1d
Fig. 1e

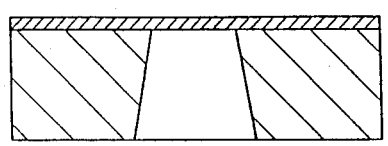
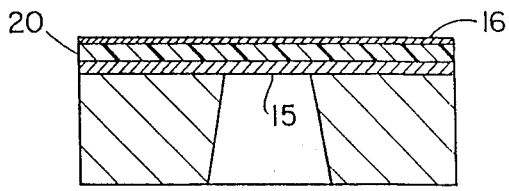
Fig. 2a   Fig. 2b
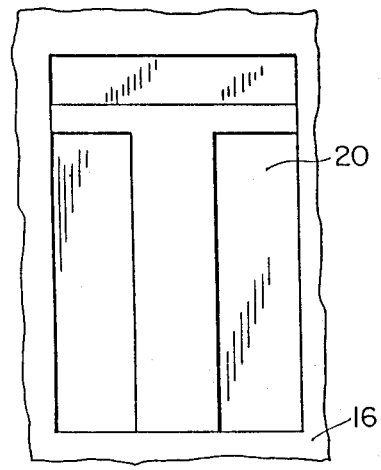
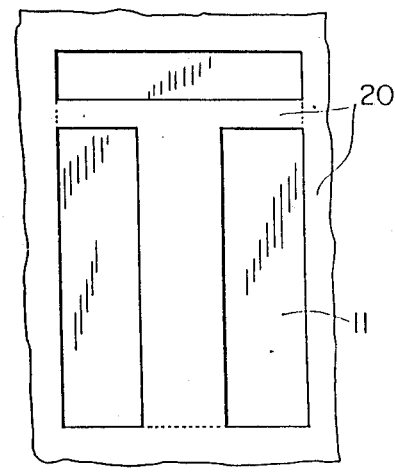
Fig. 2c   Fig. 2d
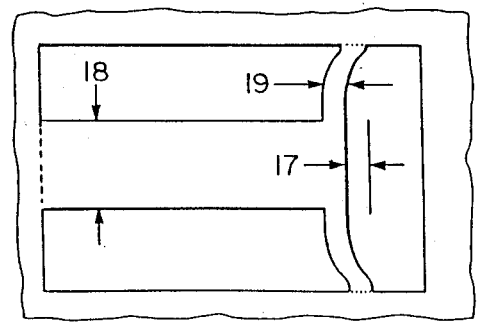
Fig. 2e

RELEASED FILM STRUCTURES AND METHOD OF MEASURING FILM PROPERTIES

BACKGROUND

This invention relates to a method of measuring the mechanical properties of films, and more particularly, to the measurement of thin films under tensile stress.

Numerous methods have been developed to determine the mechanical properties of thin films. The importance of these methods has become well known with the development of integrated circuit fabrication, packaging techniques and the recent growth in solid state sensor applications. Determining these mechanical properties is necessary in assessing the large stresses in thin films as insulating layers, which can cause cracking and adhesive or cohesive failure, leading to component failure. Stress relaxation due to creep can also alter device performance in time.

The ability to fabricate many micromechanical structures depends greatly on the mechanical characteristics of the material. Structures made of materials with tensile stress demonstrate significant performance deviation from the expected performance for the material with zero stress. For example, thin silicon diaphragm pressure sensors, in which the diaphragm is under tension, may exhibit such performance deviation.

With the increasing application of polymer films to microelectronics, it is necessary to study the mechanical properties of these films. To fully characterize the mechanical properties of a thin polymeric film material, the stress, Young's Modulus and Poisson's ratio of the film, as well as ultimate strength of the film should be determined.

Traditionally, the basic technique for measuring the stress in thin films has been to deposit the film of interest on a substrate and measure the stress-induced curvature of the substrate. See R. W. Hoffman, *Physics of Nonmetal Thin Films*, ed. Dupey and Cachard, Nato Advanced Study Institutes Service B, Vol. 14 Plenum Press, New York, 1976. The in-situ measurement of stress in polyimide films by this "wafer bending" technique was reported in P. Gelderman, C. Goldsmith, and F. Bedetti, "Measurement of Stresses Created during curing and Cured Polyimide Films," In K. L. Mittal, Ed., *Polyimides,* Plenum Press, New York, Vol. 2, 1984. The deflection or curvature of a beam supported at both ends, a cantilever beam, or a circular plate, can be measured optically by either a laser beam deflection system or by interferometric methods. The deflection can also be measured by capacitance changes or by mechanically probing the surface. See D. S. Campbell, "Mechanical properties of thin films," ed. L. I. Maissel and R. Gland, *Handbook of Thin Film Technology,* McGraw-Hill, New York, 1970.

J. W. Beams has developed a method whereby a film is deposited on a substrate and a hole is drilled in the substrate without disturbing the film. If the stress in the film is compressive, the film will bow without further pressure. The deflection of the film due to this latent compressive stress can be measured optically. To measure tensile stress using the J. W. Beams approach requires the application of pressure to the film from an external source. See J. W. Beams, eds. C. A. Neugebauer, J. B. Newkirk, and D. A. Vermilyea, *Structure and Properties of Thin Films,* John Wiley & Sons, Inc., New York, 1954.

These methods require the use of elaborate experimental instrumentation for curvature measurements, or they sacrifice accuracy and completeness to permit the use of simplified measurement methods. Reported in-situ measurement methods may rely on the buckling of microfabricated structures, which are most readily applicable to the measurement of the compressive stresses. See R. T. Howe and R. S. Muller, "Stress in Polycrystalline and amorphous silicon thin films," J. Appl. Phys. 54,4674(1983); H. Guckel, T. Randazzo, and D. W. Burns, "A single technique for the determination of mechanical strain in thin films with applications to polysilicon," J. Appl. Phys. 57,1671(1985).

SUMMARY OF THE INVENTION

A released film structure is made by first depositing a film onto a substrate, thereby inducing some intrinsic tensile stress in the film. A portion of the film is then removed to form a structure, leaving a predetermined structure whose intrinsic stress is maintained by the adhesive force of the substrate so that the structure is held in place. By removing the substrate, preferably by a plasma etch, the film structure is released or suspended permitting deformation of the structure as a result of the film's intrinsic tensile stress. By measuring the displacement of the structure from its pre-release position, it is possible to determine certain mechanical properties of the film. Most notably, the ratio of the intrinsic stress $N_0$, to Young's modulus E, of the film is easily calculated from the stress induced displacement for certain structures. Structures highly suitable for determining these mechanical properties include "T" shaped figures and fixed-end beams, as well as a rotating plate, which are illustrated in the drawings described below.

BRIEF DESCRIPTION OF THE DRAWINGS

FIG. 1 (A-E) illustrates the steps used in fabricating a substrate used in measuring film strain.

FIG. 2 (A-E) illustrates the steps used in fabricating the released structure.

DETAILED DESCRIPTION OF THE INVENTION

Figure 3:
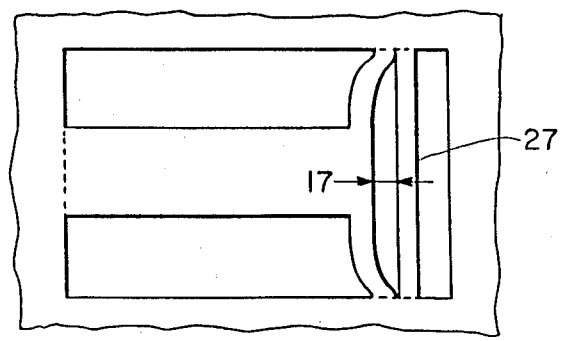
FIG. 3 is an improved "T" structure for deflection measurements using a second reference polyimide strip.

The preparation of a suitable substrate for deposition of the film whose properties are to be measured is outlined in FIG. 1. Crystalline silicon wafers have mechanical properties well suited for released structure fabrication. First, one side of the wafer 10 is doped to a thickness 11 suitable for use as a substrate (FIG. 1A). A masking material 12 is then grown or deposited on both sides of the wafer. A window 13 is opened on the back masking by a standard negative photoresist lithography (FIGS. 1B,C). The silicon substrate 10 exposed by the window is then etched 14 with a solution that will penetrate to the doped layer 11 and stop (FIGS. 1D,E). After mask removal, this doped silcon diaphragm serves as the removeable substrate 15 for released structure analysis of films.

EXAMPLE 1

The following illustrates the basic microfabrication technique for generating 3-5 micron thick silicon diaphragms used in released structure analysis.

A silicon wafer is doped with boron at 1175° C. The depth of the doping level can be adjusted by extending the deposition period, and by using an oxidizing ambient which improves boron diffusivity in silicon. A two-hour deposition yielded a 4.7 micron thick boron layer. Any thin backside doping is stripped with HF, or if more significant, by an $SF_6$ plasma or a wet chemical isotropic etch.

To avoid significant altering of the doping profile after deposition, a masking material is deposited on the surface. In this case, a thermal silicon dioxide was grown at 990° C. Oxide thicknesses were 3100A, resulting from 15 minutes dry $O_2$, 45 minutes steam at 95° C., and 15 minutes dry $O_2$.

A square window is formed in the back oxide by standard negative photoresist lithography. This is followed by a hydrazine etch at 118° C. for about 4 hours to remove the silicon through the oxide layer window. This resulted in a 1×1 mm silicon diaphragm, 4.7 microns thick, with a 2800 Å thick $SiO_2$ layer on top.

The steps for fabricating releasable thin film structures is outlined in FIG. 2. First, a diaphragm of appropriate size and thickness is fabricated as shown in FIG. 1. The masking material 12 is removed, in particular where compressive stress tends to deform the diaphragm in the material (FIG. 2A). The film 20 being evaluated is then formed on or within the substrate and covered with a material 16 suitable for masking and patterning the material (FIG. 2B). In FIG. 2C the masking material 16 is given a pattern or structure, in this case, a "T" shape. FIG. 2D illustrates the removal of the thin film 20 exposed by the structured mask. The doped substrate 11 can now be seen through the patterned masking 16 and film 20 layers. The masking layer 16 is then removed completely to permit the free suspension of the thin film when the underlying substrate 15 adjacent the film structure is etched away. FIG. 2E shows the deformation of the "T" structure resulting from substrate removal. Due to the asymmetric nature of the structure, the transverse beam of the "T" deflects 17 as a result of the intrinsic tensile stress in the base of the "T". The displacement of the structure is easily measured because the initial position of the transverse beam can be identified by drawing a straight line between the two points of the top side of the transverse beam where it meets the main portion of the film.

EXAMPLE 2

After constructing the oxide coated diaphragm of Example 1, first remove the oxide in HF. A commercially available polyimide is spin-coated onto the substrate-diaphragm using a vacuum spinning chuck at 4000 rpm for 2 minutes. (Note that films whose properties are to be measured can also be deposited by spraying, spreading, painting, evaporating, sputtering, chemical vapor depositing (CVD), or by applying with any other suitable method.) This results in a film thickness of 2.5 microns. This layer is then baked at 135° C. for 14 minutes. These coating and baking steps may be repeated to produce a film of desired thickness. In this case, 4 layers are applied, resulting in a 10 micron thick film which is then post-baked at 436° C. for 45 minutes.

To pattern the film, an aluminum layer of 2000 Å is first evaporated onto the polyimide surface. The desired pattern is placed on the aluminum surface by a negative resist lithography. The aluminum pattern is first removed by a plasma etch. This reveals the surface of the polyimide through the patterned aluminum. The polyimide, as well as removal of the negative resist material, is accomplished by an $O_2$ plasma etch. The aluminum layer is then removed using either a $CCl_4$ plasma or a wet chemical etch, such as a Phosphoric-Acetic Nitric Acid solution.

The final step is to release the structure by removing the silicon diaphragm. To remove a 4.7 micron thick diaphragm, a $SF_6$ plasma etch is applied to the back of the diaphragm for 10 minutes.

The "T" shape is particularly useful in measuring the ratio of residual stress to modulus. Large deflections are observed without creating large strains in the main body of the film surrounding the released structure. This guarantees that the film is in its linearly elastic domain. If the dimensions of the structure are selected appropriately, the Poisson's ratio for the film can also be extracted.

In the discussion to follow, a simple analysis of the structure is performed by making appropriate assumptions, which can be verified later. FIG. 2E describes the parameters. This structure is modeled as a fixed-end beam or width 19, uniformly loaded in the center region by the center leg of width 18. The stress-induced shrinkage of this center leg creates the uniform load on the beam. To analyze this indeterminate structure, the force per unit length q on the boundary, is found in terms of the center deflection, d, (see deflection 17 of FIG. 2E) when the structure is released.

The dimensions of the structure can be appropriately selected such that the deflection of the polyimide beam, d, is always less than 30% of the beam width, h. In this case, the beam deflections can be found by the well known application of small deflection theory and where the membrane stresses created as a result of the stretching of middle plane of the beam can be neglected. In this derivation, the effect of the residual tensile stress in the transverse beam is also neglected.

The center deflection of a fixed-end beam under uniform load over a region in the center can be found by superposition of the deflections due to bending and shear as:

$$d = d_b + d_s, \qquad (1)$$

where d is the total deflection and $d_b$ and $d_s$ are the contributions from bending and shear, respectively. The deflection at the center due to bending $d_b$ is given by:

$$d_b = \frac{qW}{192EI}\left(L^3 - W^2L + \frac{W}{2}\right) \qquad (2)$$

where $$I = bh^3/12 \qquad (3)$$

L is the length of the beam, b is the film thickness, W is the center leg width (18 in FIG. 2) and E is Young's Modulus.

The component of the deflection due to shear, $d_s$, given by $$d_s = \frac{a_s q W}{4GA}\left(L - \frac{W}{2}\right), \quad (4)$$

where $$A = bh \quad (5)$$

$a_s$ is the shear coefficient (which is equal to 1.5 for a beam with rectangular cross-section) and G is the modulus of elasticity in shear. The total deflection is:

$$d = d_b + d_s = q\left[\frac{W}{192EI}\left(L^3 - W^2L + \frac{W^3}{2}\right) + \frac{a_s W}{4GA}\left(L - \frac{W}{2}\right)\right]. \quad (6)$$

Note that shear forces aid deflection.

However, q, is the load that is generated by stress-induced shrinkage of the center leg and is given as:

$$q = bE\left(\frac{N_0}{E} - \frac{d}{L_1}\right) \quad (7)$$

where $N_0$ is the residual tensile stress, $L_1$ is the length of the center leg. In truth, this parameter is $$L_{10} = \frac{L_1}{1 + \frac{N_0}{E}} \quad (8)$$

where $L_{10}$ is the length of the presumably stress free transverse beam. However, this correction is of second order and is neglected here. In finding q, the center leg stress-induced shrinkage is modeled as uniform across the width, W. In reality, due to the curvature in the beam, this is not the case. However, the length of the center leg is very large compared to the variation in shrinkage across the width and justifies the assumption. By substituting equation (7) into equation (6) the ratio of the stress to the modulus is related to the deflection, d, the dimensional parameters, and Poisson's ratio u as $$d = \left(\frac{N_0}{E} - \frac{d}{L_1}\right)\left[\frac{W}{16h^3}\left(L^3 - W^2L + \frac{W^3}{2}\right) + \frac{3W(1-u)}{4h}\left(L - \frac{W}{2}\right)\right]. \quad (9)$$

Note that the first term in the bracket in equation (9) is the contribution due to bending moment while the second term is the contribution due to shear. The bending term is approximately proportional to cubic ratio of the beam length to the beam width while the shear term is proportional to the first power of the same ratio. If the fixed-end beam is made slender (large ratio of the beam length, L to the beam width, h) the contribution of the shear component is negligible. This contribution, however, is large for stocky beams, which are beams for which the ratio of L to h is not large. For a ratio of length to width of the beam larger than 10, the shear component is less than 10%. In this case, the shear contribution is neglected to simplify equation (9) to:

$$\frac{N_0}{E} = d\left[\frac{1}{L_1} + \frac{16}{W\left(\frac{L^3}{h^3} - \frac{W^2L}{h^3} + \frac{W^3}{2h^3}\right)}\right] \quad (10)$$

By fabricating a structure of appropriate dimensions on a silicon diaphragm and then removing the diaphragm to release the structure, the deflection d can be measured. Using equation (10), the ratio of the stress to the modulus can be calculated. In addition, if several beams with small ratios of length to width are fabricated on the same sample, equation (10) can be used to fit the data and extract the values of $N_0/E$ and u that best fit.

EXAMPLE 3

Two wafers were processed with BTDA-MDA/ODA (benzo phenonetetracarboxylic dianhydride-oxydianiline/metaphenylene diamine), a microelectronic grade polyimide of thicknesses 5.5 and 8.0 microns. Each wafer had several T structures with either slender of stocky beams. The deflections are measured with ±3 microns accuracy using an optical microscope. For the slender beam structures (ratio of the length to width of the beam above 10), equation (10) was used to find the stress to modulus ratio. All the fabricated structures have a beam length, L, of 2048 microns. Table I presents the data, including the critical dimensions, for the wafer with 5.5 micron thick film. The ratio of the stress to the modulus is 0.011±0.002. It is evident from equation (10) that the error in measuring d creates the uncertainty in the calculated stress to modulus ratio. In this work, the error in measuring the deflection, d, is at least 10% (increasing for smaller deflections). This large measurement error translates into the error on the calculated stress to modulus ratio. The reason for the large measurement error is that measurements had to be taken at low magnification to be able to see the entire fixed-end beam portion in the field of view of the microscope. At higher magnification where the accuracy of the measurement increases, the entire beam is not in the field of view to provide a reference for measuring the deflection.

TABLE I

Data on Slender-Beam T Structures

| # | W | h | $L_1$ | d | $\frac{N_0}{E}$ |
|---|---|---|---|---|---|
| 1 | 800 | 133 | 3027 | 35.0 | 0.0118 |
| 2 | 800 | 133 | 4027 | 42.5 | 0.0108 |
| 3 | 800 | 133 | 4027 | 40.5 | 0.0102 |
| 4 | 800 | 166 | 4027 | 37.0 | 0.0097 |
| 5 | 500 | 166 | 3027 | 30.0 | 0.0104 |
| 6 | 500 | 166 | 3027 | 33.0 | 0.0116 |
| 7 | 500 | 209 | 3027 | 30.0 | 0.0110 |

(W, h, $L_1$ and d are in microns)

Note that as the length to width ratio for the beam is decreased to enhance the shear contributions, the percent uncertainty in the deflection measurements increase since the deflections decrease. One way to improve the deflection measurement is to put a straight strip 27 of the polyimide close to the front of the beam as shown in FIG. 3. This allows for going to high optical magnification since it is no longer necessary to have the whole beam in the field of view. However, it is unlikely that measurements with better than ±1 micron accuracy can be performed using an optical set up. A potential method is the use of diffractometry through the slit created by the strip and the deflected beam. This would improve the accuracy in measuring the deflection to fractions of a micron.

Other structures that are well suited for measuring the mechanical properties of thin polyimide structures are shown in FIG. 4(A–H) both before and after release from the substrate. In FIG. 4A, the square polyimide plate in the center rotates after release FIG. 4B because of the stress-induced shrinkage of the four arms 29, acting as two pairs of couples. In FIG. 4C, the fixed end polyimide beam deflects due to stress-induced shrinkage of the five arms 30 (FIG. 4D), creating a uniform load over parts of the beam. In FIG. 4E, the square plate held by four legs 31 and a wide center arm deflects as shown in FIG. 4F due to the stress-induced shrinkage of the long center arm, pulling on the plate. FIG. 4G shows a fixed-end polyimide beam with an abrupt width-change at a selected point 28 along the axis of the beam. Upon release of the structure in FIG. 4H the width-change boundary is displaced due to force imbalance in the structure. The wide portion shrinks, stretching the thinner members until force balance is achieved.

Figure 5:
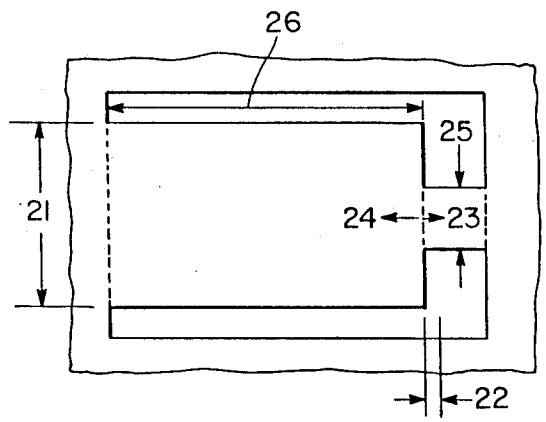
FIG. 5 shows the parameters for the fixed-end beam analysis.

These fixed-end beam structures are particularly useful in studying the ratio of the intrinsic stress in the film to the modulus, the yield strain, and the ultimate strain at break. The analysis is simple and demonstrates how the above parameters can be measured. FIG. 5 describes the parameters. Since the whole structure is made of the same material with uniform thickness, b, the depth dimension is incorporated here by introducing forces per unit length. This automatically assumes that the stresses are uniform across the thickness of the film. All the parameters of the wide member are denoted with subscript 1 while the parameters of the thin members are denoted with subscript 2.

This indeterminate structure is analyzed by assuming a displacement d (22 in FIG. 5) after the structure is released. Then, the force, $F_1$, acting on the boundary by the stress-induced shrinkage of the wide member is $$F_1 = EW_1 \left( \frac{N_0}{E} - \frac{d}{L_1} \right) \tag{11}$$

where E is the Young's modulus, $N_0$ is the residual stress in the film, $L_1$ is the initial length of the wide member, and $W_1$ is the width of the wide member. The force, $F_2$, acting on the boundary because of the stretching of thin members due to the shrinkage of the wide member is $$F_2 = EW_2 \left( \frac{N_0}{E} + \frac{d}{L_2} \right) \tag{12}$$

where $L_2$ and $W_w$ are the length 23 and width 25 of the thin member. At equilibrium the two forces are equal. Setting equations (11) and (12), the result is $$\frac{N_0}{E} = d \left( \frac{\frac{W_1}{L_1} + \frac{W_2}{L_2}}{W_1 - W_2} \right) \tag{13}$$

Figure 4A:
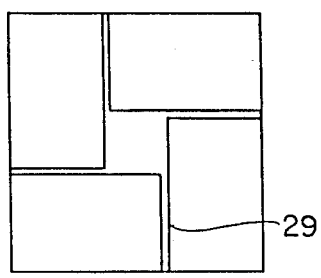
FIG. 4 (A-H) shows a series of structures used in evaluating polyimide tensile stress.
Figure 4B:
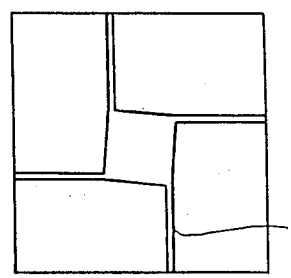
Figure 4C:
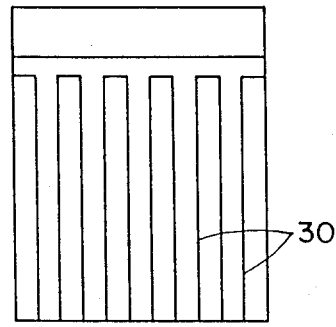
Figure 4D:
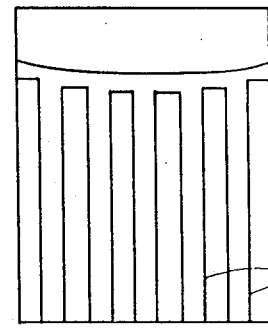
Figure 4E:
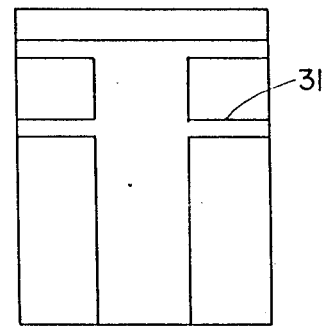
Figure 4F:
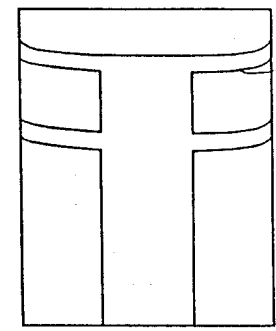
Figure 4G:
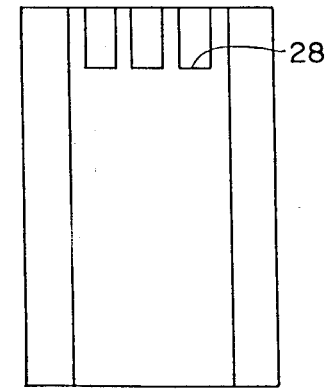
Figure 4H:
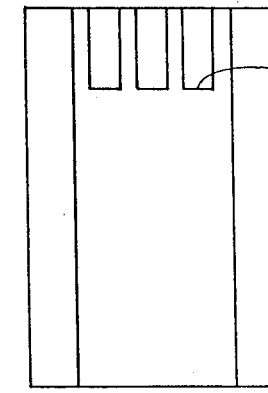
Figure 6:
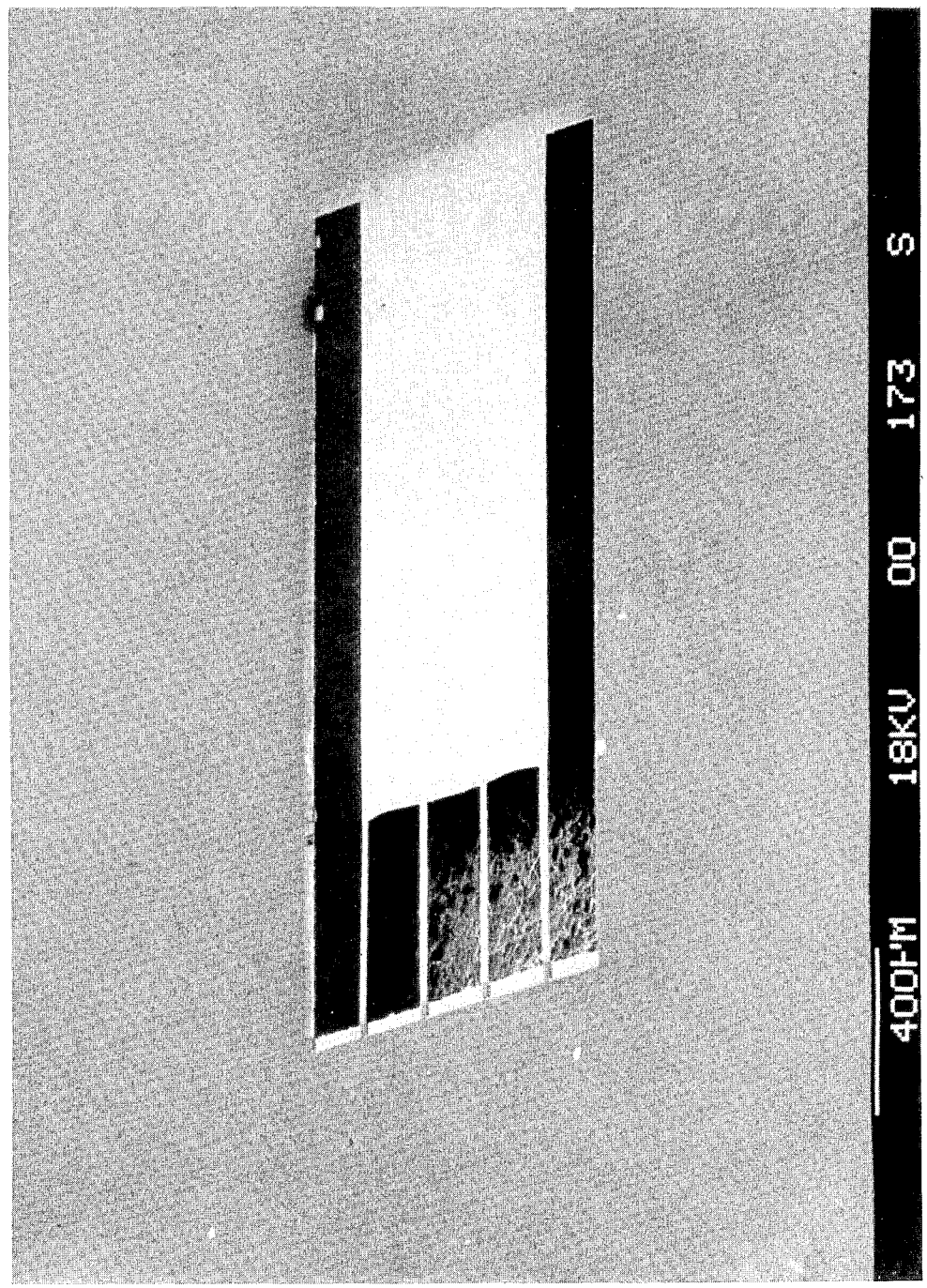
FIG. 6 is a photomicrograph of a fixed-end beam structure after release.

For actual fabrication, the thin member is split into two or four thinner members placed at equal distances across the width of the boundary (FIG. 4G and FIG. 6). This avoids the out of plane curling of the edges, that otherwise would be unsupported, and greatly improves the stability of the structure. However, the above analysis still applies as long as $W_2$ is taken to be the total width of the thinner members.

In the above analysis, $L_1$ and $L_2$ are the lengths of the members before releasing the structure. In truth, these should be the length of the members, $L_{01}$ and $L_{02}$, when the members are stress-free. For example, the relationship between $L_1$ and $L_{01}$ is:

$$L_{01} = \frac{L_1}{1 + \frac{N_0}{E}} \tag{14}$$

However, this correction is of second order and is neglected here.

Equation (13) shows that by measuring the displacement d after the structure is released, the ratio of the stress to modulus can be determined. It is also clear that the strain in the thin arms, e is $$e = \frac{N_0}{E} + \frac{d}{L_{02}} = \frac{N_0}{E} \left( 1 + \frac{d}{L_2} \right) + \frac{d}{L_2} \tag{15}$$

Figure 10:
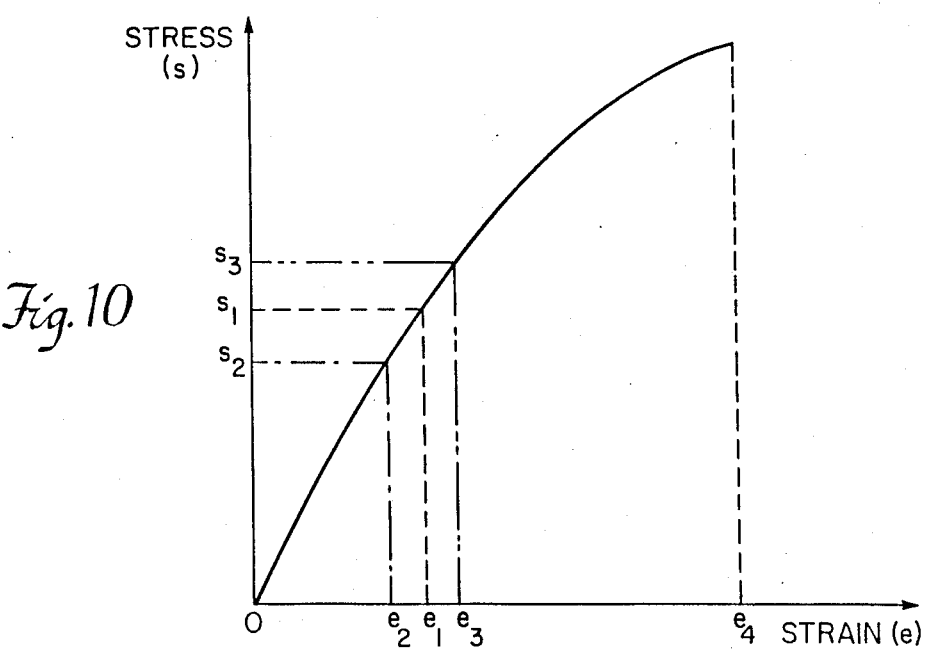
FIG. 10 is a schematic graph showing the relationship between stress and strain for a film.

By appropriate selection of dimensions, the e can range from nearly zero to the ultimate strain at break. In this way, the beams can function like a tensile testing machine. The modulus can be studied as a function of strain since the residual stress is constant, to find the ultimate strain for the film. Coupled with stress measurements from load-deflection studies on polyimide membranes, the stress-strain curve can be determined. Such a curve is schematically illustrated in FIG. 10, in which $S_1$ and $e_1$ are the stress and strain of the films as fabricated. Known methods of stress analysis, such as the cantilever beam yield only $S_1$ and $e_1$ for a particular film. By varying the dimensions of the structures, the strain can be varied over a range of values $e_2$, $e_3$ including the ultimate strain at break $e_4$. This aspect of the invention arises due to the redistribution of stress that occurs upon release of the structure. For example, by varying the width of the narrow beams, the structure will deform differently upon release yielding a different strain e.

EXAMPLE 4

Two wafers were processed, with polyimide film thickness of 5.5 microns for the first sample and 8.5 microns for the second. Beams with various dimensions were fabricated on each sample. Table II shows the data on six beams that were fabricated on the wafer with 5.5 micron polyimide film. The deflections were measured with ±3 microns accuracy.

TABLE II
Data on Fixed-end Beam Structures

| $L_1$ | $L_2$ | $W_1$ | $W_2$ | d | $\frac{N_0}{E}$ |
|---|---|---|---|---|---|
| 1535 | 505 | 690 | 2 × 45 | 13.0 | 0.0136 |
| 1535 | 505 | 690 | 2 × 45 | 13.0 | 0.0136 |
| 1535 | 505 | 690 | 4 × 20 | 14.0 | 0.0140 |
| 2510 | 505 | 590 | 2 × 95 | 11.5 | 0.0151 |
| 2510 | 505 | 690 | 2 × 95 | 12.0 | 0.0156 |
| 2510 | 505 | 690 | 4 × 45 | 12.0 | 0.0149 |

($L_1$, $L_2$, $W_1$, $W_2$, and d are in microns)

The stress to modulus ratio for these samples is 0.0145±0.002, somewhat higher than expected. There are two explanations: first, the stress in the polyimide film of this wafer is higher than normally observed. Second the film could have yielded since the strains are high, on the order of 4%. On the wafer with the thinner film, when the strain, $e_2$, exceeded 4.5%, the members completely failed. On the wafer with the thicker polyimide film, although the film cracked above 4.5% strain, it did not break until 8% strain was reached. Ratio of the stress to modulus calculated from measurements on this sample are also in agreement with the above results for strains close to 4.5%. The ratio increased for higher strains, which is attributed to the cracking of the film, acting like the film is yielding. In a thin film, cracks are fatal while in the thicker film the cracks provide partial relaxation of the stress in the member. Even though there is not enough data for a firm conclusion, it may be assumed that the film is yielding at strains close to 4%. To confirm this, the stress to modulus ratio has to be determined for this film at lower strains. This can be done by either adjusting the dimensions of the structures or putting T structures on the sample.

Figure 7:
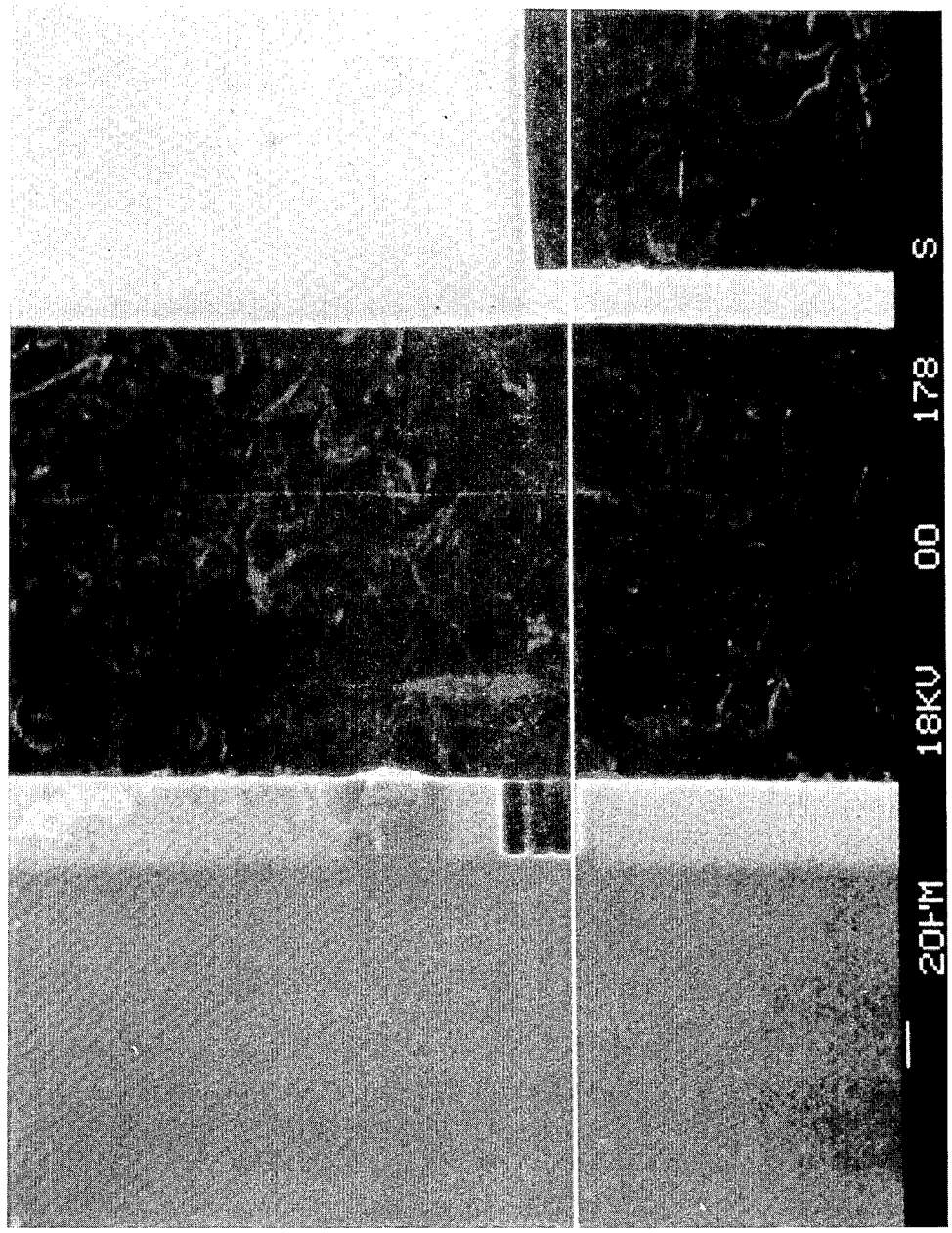
FIG. 7 is a photomicrograph of a magnified view of the displaced width-change boundary shown in FIG. 6.

FIG. 6 shows a SEM photograph of a typical fabricated beam on the 5.5 micron thick polyimide sample. The dimensions are 1500 microns long by 490 microns wide, changing to 80 microns wide (20 microns for each member) for a length of 505 microns. FIG. 7 is the magnified view of the boundary in the FIG. 6. The white line marks where the width-change boundary was located before the structure was released. The displacement in this case is 14 microns.

Figure 8:
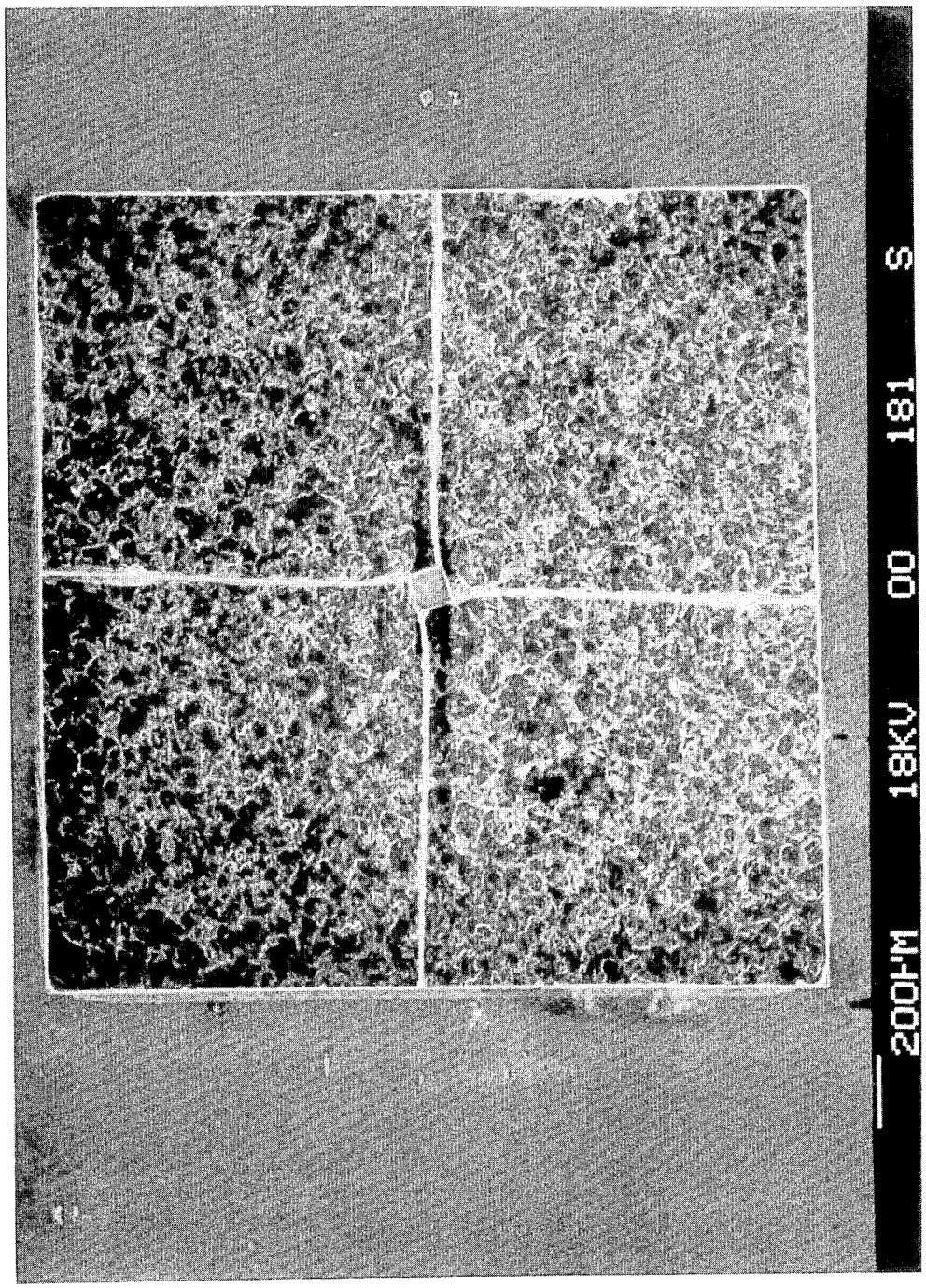
FIG. 8 is a photomicrograph of a rotated polyimide film

FIG. 8 is a SEM photograph showing a rotated plate after release that is held by four orthogonal arms.

Figure 9:
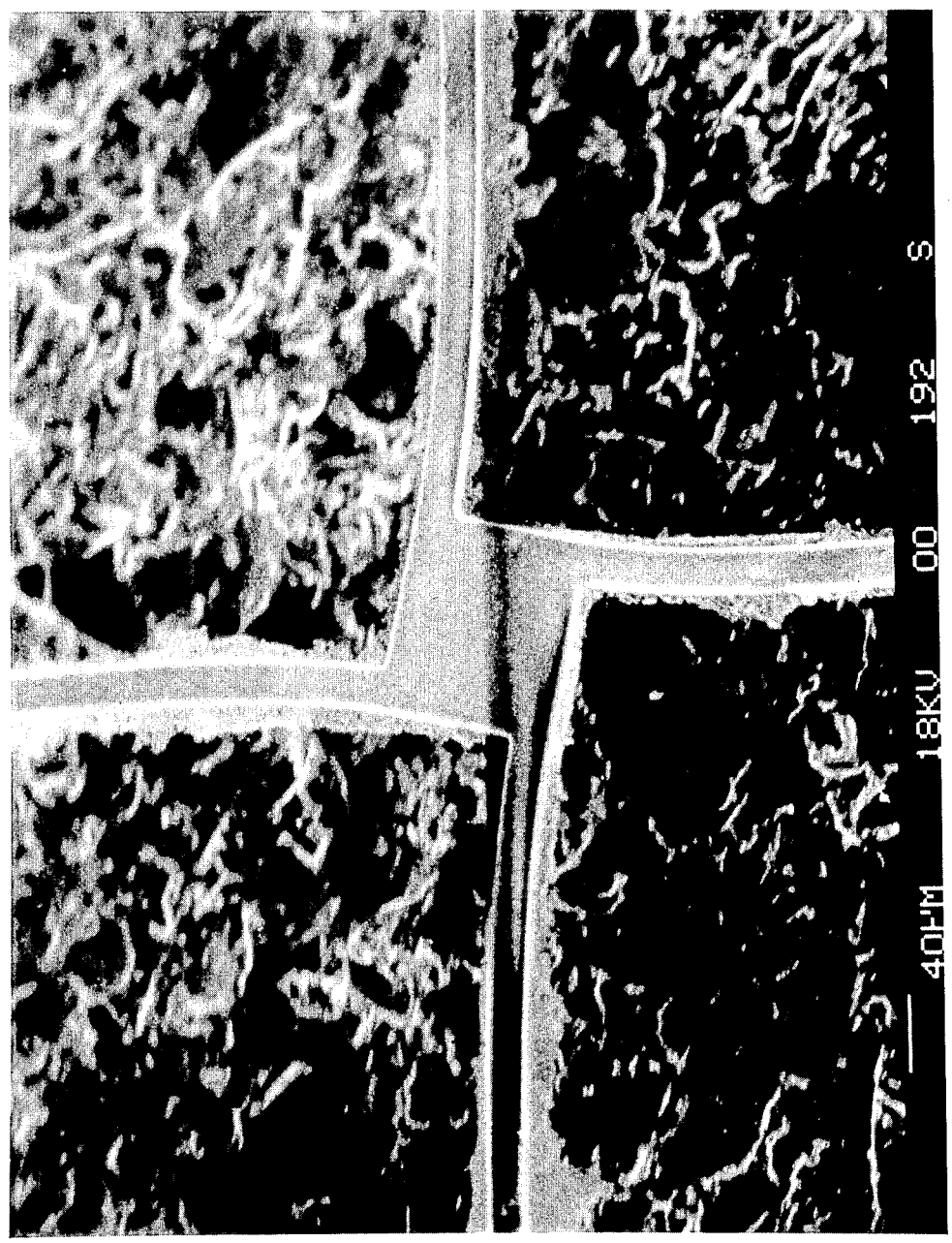
FIG. 9 is a magnified view of the rotated plate shown in FIG. 8.

FIG. 9 is a magnified view of the plate.

In summary, beam dimensions were chosen to study a variety of polyimide chemistries with BTDA-ODA/MPDA being the first to try. This polyimide develops failure signs at strains above 4.5% and fails at above 8% strain (for 8.5 micron thick film). The ultimate strains for BTDA-ODA/MPDA polyimide were thought to be above 10%. The fixed-end beam structures are appropriate for studying both the stress to modulus ratio at high strains and the ultimate strain of thin films under tension have been introduced. These structures can be used in-situ with accurate control on the dimensions and axial loading of the beam. The film can be viewed in-situ as strained with optical and scanning electron microscopes, revealing failure signs such as cracking.

While the invention has been particularly shown and described with reference to preferred embodiments thereof, it will be understood by those skilled in the art that various changes in form and details may be made without departing from the spirit and scope of the invention as defined in the appended claims.

We claim:

1. A method of measuring film strain comprising:
   forming a bridged film structure on a substrate such that residual tensile stress induced in the structure is maintained by the substrate;
   recording the position of the structure;
   releasing the film structure from the substrate such that the residual stress deforms the structure; and
   measuring the displacement of the structure from its recorded position.

2. A method of measuring film strain as defined in claim 1 wherein said measured displacement is used in calculating the ratio of the intrinsic stress, $N_0$, to Young's modulus, E, for the film.

3. A method of measuring film strain as defined in claim 2 wherein the displacement and said ratio are used in calculating the strain in the displaced film structure.

4. A method of measuring film strain as defined in claim 3 wherein the ultimate strain for the film is determined.

5. A method of measuring film strain as defined in claim 2 wherein a multiplicity of various film structures are measured to yield correlative values for the ratio of intrinsic stress to Young's modulus for each film structure.

6. A method of measuring film strain as defined in claim 2 wherein Poisson's ratio for the film is determined.

7. A method of measuring film strain as defined in claim 1 wherein said film structure is comprised of:
   a main body of the film;
   a first beam attached at both ends to the main body; and
   a second beam bisecting at a right angle and attached at one end to the first beam, and attached to the opposite end to said main body.

8. A method of measuring film strain as defined in claim 1 wherein said film structure is comprised of:
   a main body of the film; and
   a central member with at least first and second supporting members extending in opposite directions from the central member to the main body.

9. The method of measuring film strain as defined in claim 1 further comprising the step of measuring a plurality of bridged film structures to determine the relationship between stress and strain for the film.

10. A releasable structure comprising:
    a substrate; and
    a film formed on the substrate having a main body and a bridge structure with intrinsic tensile stress such that the structure is maintained by the substrate and is releasable from the substrate such that the structure deforms.

11. A releasable structure as defined in claim 10 wherein said structure is comprised of a first beam attached at both ends to the main body of the film, and a second beam bisecting at a right angle and attached at one end to the first beam, and attached at the opposite end to said main body.

12. A releasable structure as defined in claim 10 wherein said structure is comprised of a central member with at least first and second supporting members extending in opposite directions from the central member to the main body.

13. A releasable structure as defined in claim 12 wherein said central member and said first supporting member form a rectangle that is wider than the second supporting member that is rectangular.

14. A releasable structure as defined in claim 12 wherein said central member and one supporting member form a rectangle having a multiplicity of oppositely extending supporting members such that the width of the rectangle is wider than the aggregate width of said oppositely extending members.

15. A releasable structure as defined in claim 12 wherein said central member is rotatable with four orthogonally extending supporting members which are attached at one end to the main body and at the opposite end to the central member.

16. A method of measuring the relationship between stress and strain in films comprising the steps of:
   forming a plurality of bridged film structures on a substrate having residual tensile stress such that each structure has a different geometry;
   releasing each structure from the substrate such that each structure is displaced by the residual stress; and
   measuring the displacement of each structure.

17. The method of claim 16 further comprising the step of determining the relationship between the stress and strain of the film.

* * * * *